United States Patent [19]

Bolesky et al.

[11] Patent Number: 5,002,577
[45] Date of Patent: Mar. 26, 1991

[54] VARIABLE POSITION ACETABULAR CUP

[75] Inventors: Richard C. Bolesky; Maureen A. MacCollum, both of Warsaw, Ind.

[73] Assignee: Boehringer Mannheim Corporation, Indianapolis, Ind.

[21] Appl. No.: 392,430

[22] Filed: Aug. 10, 1989

[51] Int. Cl.[5] .............................................. A61F 2/32
[52] U.S. Cl. ..................................................... 623/22
[58] Field of Search ....................... 623/16, 18, 19, 20, 623/22, 23

[56] References Cited

U.S. PATENT DOCUMENTS

| | | | |
|---|---|---|---|
| 2,765,787 | 10/1956 | Pellet | 623/22 |
| 3,829,904 | 8/1974 | Ling et al. | 623/22 |
| 4,123,806 | 11/1978 | Amstutz et al. | 623/22 |
| 4,327,449 | 5/1982 | Charnley | 623/22 |
| 4,385,405 | 5/1983 | Teinturier | 623/22 |
| 4,437,193 | 3/1984 | Oh | 623/22 |
| 4,623,351 | 11/1986 | Church | 623/22 |
| 4,623,352 | 11/1986 | Oh | 623/22 |
| 4,650,491 | 3/1987 | Parchinski | 623/22 |
| 4,678,472 | 7/1987 | Noiles | 623/22 |
| 4,695,282 | 9/1987 | Forte et al. | 623/22 |
| 4,822,370 | 4/1989 | Schelhas | 623/22 |

FOREIGN PATENT DOCUMENTS

| | | |
|---|---|---|
| 163920 | 12/1985 | European Pat. Off. . |
| 241361 | 10/1987 | European Pat. Off. . |
| 295360 | 1/1988 | European Pat. Off. . |
| 285756 | 2/1988 | European Pat. Off. . |
| 764438 | 12/1956 | United Kingdom . |
| 1409051 | 10/1975 | United Kingdom . |
| 2068734 | 8/1981 | United Kingdom . |

Primary Examiner—David J. Isabella
Attorney, Agent, or Firm—Barnes & Thornburg

[57] ABSTRACT

A variable position acetabular cup assembly for replacing a natural hip socket includes a symmetrical base cup, a symmetrical polymer bearing, and a nonsymmetrical adapter ring situated between the base cup and the bearing. The base cup is designed to be affixed to the acetabulum to replace the natural socket. The bearing provides a bearing surface for receiving a femur ball. The adapter ring can be mounted on the base cup in a plurality of positions to change the position of the symmetrical bearing after the base cup is secured to the acetabulum.

31 Claims, 2 Drawing Sheets

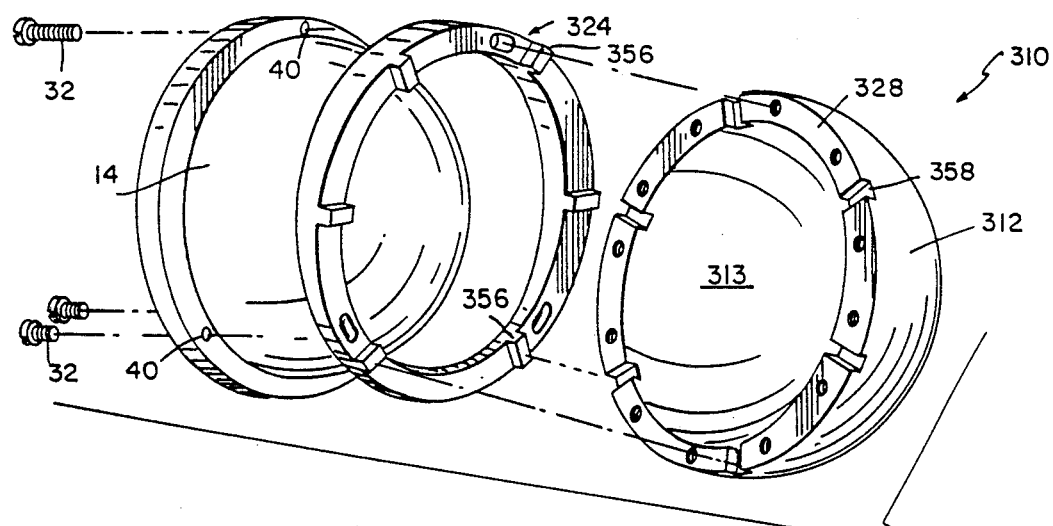
FIG. 5
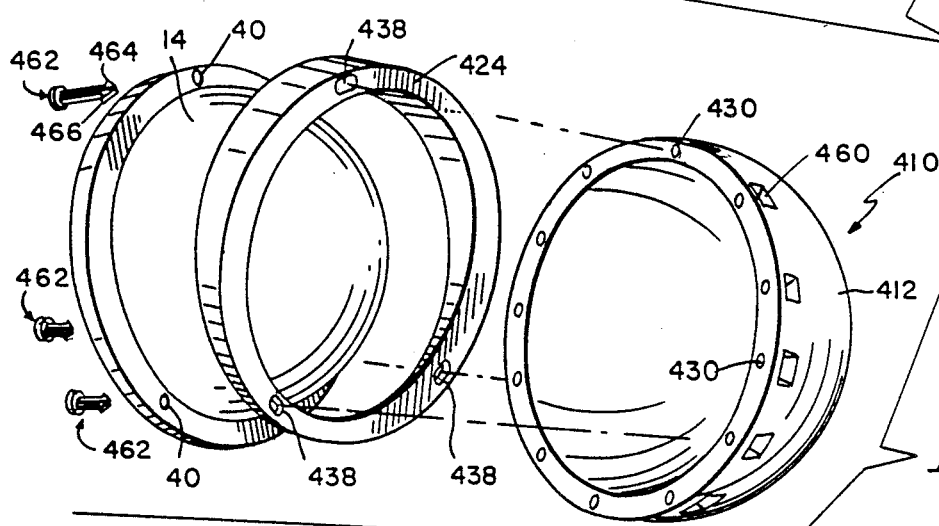
FIG. 6
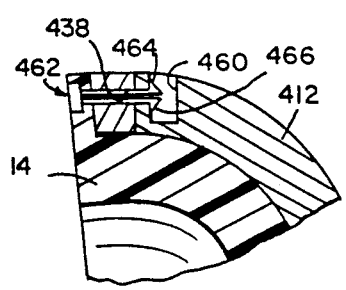
FIG. 7
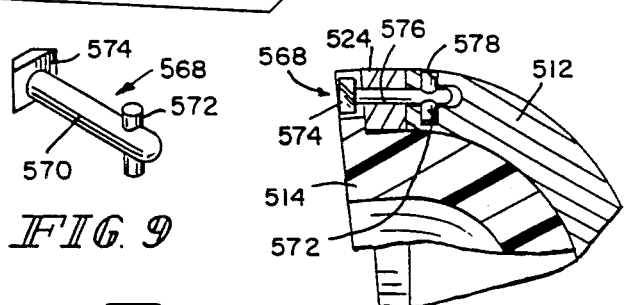
FIG. 9
FIG. 8
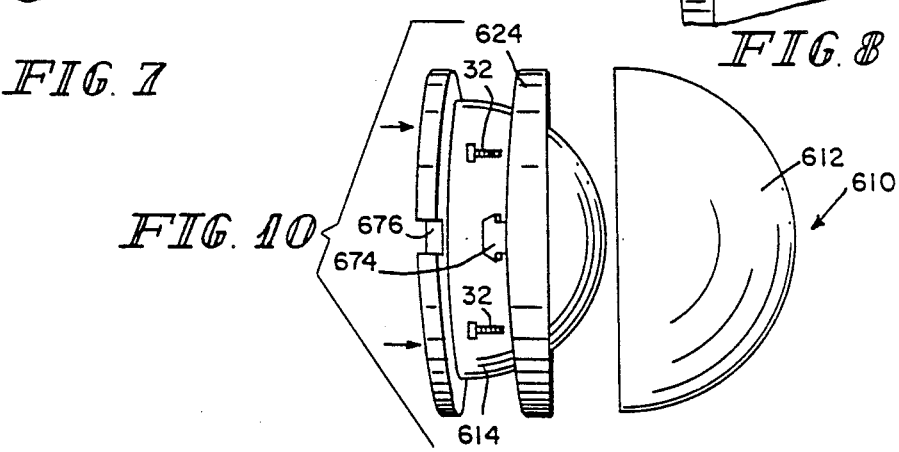
FIG. 10

VARIABLE POSITION ACETABULAR CUP

The present invention relates to hip prosthesis assemblies, and more particularly to the provision of an acetabular cup assembly having a polymer bearing which can be presented in a plurality of selectively variable positions relative to the acetabulum. The present invention provides an acetabular cup assembly comprising a base cup which is to be affixed to the acetabulum to replace the socket, a polymer bearing which is received in the cup to provide a hemispherical bearing for receiving the femur ball prosthesis element, and an adapter ring or mounting means for mounting the bearing in a plurality of selected positions about the base cup. It is the adapter ring or mounting means which varies the position of the polymer bearing. The base cup and the polymer bearing may both preferably be symmetrical. The adapter ring or mounting means is preferably non-symmetrical such that, when it is mounted on the base cup in selectively variable positions, it will present the symmetrical bearing in various positions relative to the acetabulum and base cup. In this manner, the orthopedic surgeon installing the hip prosthesis can rather easily and confidently position a symmetrical bearing in a plurality of positions better to receive the femur ball after the base cup is firmly affixed to the acetabulum.

DESCRIPTION OF PRIOR ART

It is known in prior art hip prosthesis assemblies to use asymmetric acetabular cups to provide a bearing surface for the femur ball. These acetabular cups are cemented directly to the acetabulum to replace the natural socket of the hip joint. Typically, it takes several minutes for the cement used to attach the acetabular cup to the acetabulum to set. During this setting time, the surgeon is able to change the position of the acetabular cup to obtain a preferred orientation for the bearing portion of the cup which receives the femur ball.

Attempts have also been made to change the angle of the shaft leading from the stem implanted in the femur to the femur ball in order to provide better engagement of the femur ball with the bearing surface of the acetabular cup assembly. Examples of prior art devices which change the angle of the shaft of the femur ball connection are shown in such prior patents as U.S. Pat. No.(s.) 2,765,787 and 4,822,370.

Other acetabular cup assemblies use non-symmetrical bearings which fit selectively inside symmetrical base cups so that the position of the non-symmetrical bearing can be changed after the base cup is fixed to the acetabulum. Cup assemblies using non-symmetrical bearings are more expensive to manufacture because the non-symmetrical bearings are difficult to hold within the tolerances required by prosthetic devices. In addition, non-symmetrical bearings produce stress concentrations at the point of the highest loads. Acetabular cup assemblies using non-symmetrical bearings are shown in such prior patents as U.S. Pat. No(s). 4,650,491; 4,695,282; and 4,678,472.

SUMMARY OF THE INVENTION

The present invention constitutes an improvement over the prior art for several reasons. The preferred symmetric polymer bearing has relatively fewer stress concentrations than will occur in a tapered or built-up bearing such as those shown in the prior art. The preferred bearing material used in prosthesis devices is typically a polymeric material, e.g., ultra high molecular weight polyethylene (UHMWPE) Such poly material will have serious stress concentrations anytime the thickness of the material changes. Providing a thicker or non-symmetrical lip on such a bearing as shown in the prior art will produce detrimental stress concentrations at the point of the highest loads. In the present invention, the area of increased coverage of the ball or overhang of the bearing is supported by the metal adapter ring or mounting means, and not supported merely by the build up of the polymeric material. Further, with a selectively movable metal adapter ring, the physician can see the orientation and coverage provided by the metal ring prior to the insertion of the symmetric polymer bearing.

Further, in the process of manufacturing a polymeric bearing, any complex shapes are difficult to manufacture and even more difficult to hold within the tolerances required by prosthetic devices. Thus, the polymeric bearing with the built-up overhang or non-symmetry shown in the prior art is much more difficult to manufacture because of tolerance problems. In the present invention, the use of a metal adapter ring with a symmetrical polymeric bearing greatly facilitates the tolerance requirements.

It is an object of the present invention, therefore, to provide an acetabular prosthesis comprising a base cup for attachment to the acetabulum to replace the natural socket, bearing means for holding a femoral ball in the base cup, means for mounting the bearing means on the base cup, and means for attaching the mounting means in a plurality of selected positions on the base cup. The mounting means or adapter ring as it is sometimes referred to herein is non-symmetrically shaped such that it will selectively position and present the bearing means on the base cup. In this fashion, a symmetrical polymeric material bearing with a symmetrical hemispherical cavity for receiving the ball will be non-symmetrically presented on the acetabulum.

Another object of the present invention is to provide such a prosthetic assembly in which the base cup has a symmetrical, generally hemispherical cavity open toward the ball which is mounted on the femur and the polymer bearing is disposed in the cavity of the base cup to provide a hemispherical bearing surface for the ball. In this structure, the mounting means or adapter ring is mounted on the base cup about its cavity to position the symmetrical bearing in selected positions relative to the base cup. The mounting means or adapter ring may be generally wedge-shaped with a plane surface to mount against the base cup and an inclined plane surface against which the polymer bearing mounts. Thus, in its various selected positions on the base cup, the ring will alter the position of the bearing relative to the axis of the base cup.

Other objects and features of the present invention will become apparent as this specification proceeds.

BRIEF DESCRIPTION OF THE DRAWINGS

FIG. 5 is an exploded perspective view of another embodiment of the present invention in which the adapter ring includes a plurality of lugs configured to be received by notches formed in the base cup;

FIG. 6 is an exploded perspective view of yet another embodiment of the present invention which uses clips to secure the bearing and the adapter ring to the base cup;

FIG. 7 is a sectional view of the embodiment of the invention shown in FIG. 6 illustrating a clip in its locked position;

FIG. 8 is a sectional view of still another embodiment of the present invention using a bayonet and castellation fastener to secure the bearing and the adapter to the base cup;

FIG. 9 is a perspective view of the bayonet and castellation fastener used to secure the bearing and adapter ring to the base cup in the embodiment shown in FIG. 8; and FIG. 10 is a side view of a further embodiment of the present invention in which a castellation is formed directly on the adapter ring for securing the bearing to the adapter ring.

DETAILED DESCRIPTION OF THE DRAWINGS

Figure 1:
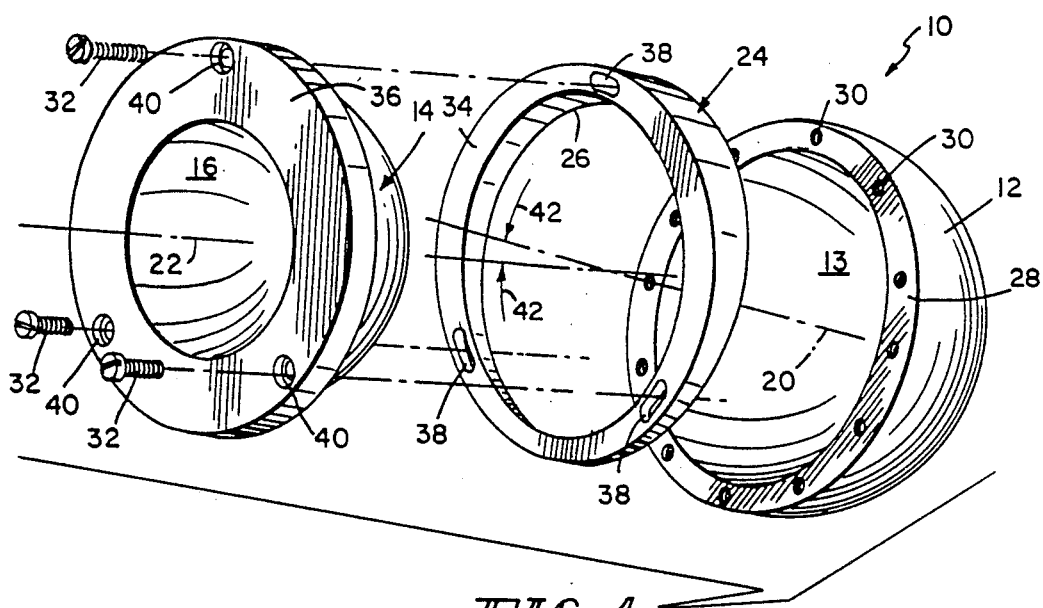
FIG. 1 is an exploded perspective view of a variable position acetabular cup assembly according to the present invention.
Figures 2, 3:
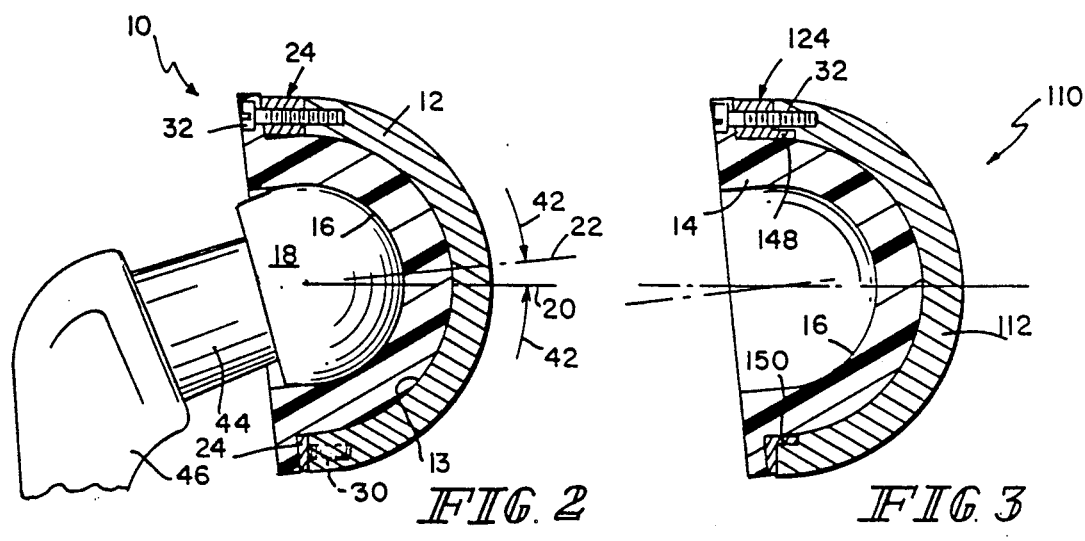
FIG. 2 is a sectional view of the acetabular cup assembly showing a ball inserted into a bearing.
FIGS. 3 and 4 are sectional views of two additional embodiments of the acetabular cup assembly showing two track configurations for simplifying rotation of the adapter ring relative to the base cup.

Referring now to the drawings, FIG. 1 illustrates a variable position acetabular cup assembly 10 according to the present invention. The cup assembly 10 includes a base cup 12 designed to be affixed to the acetabulum to replace the natural hip socket. The base cup 12 includes a cavity 13 for receiving a polymer bearing 14. Bearing 14 provides a hemispherical bearing surface 16 for receiving a femur ball 18 as best shown in FIG. 2.

Referring again to FIG. 1, the base cup 12 is symmetrical about an axis of symmetry 20 through the center of base cup 12. Bearing 14 is also symmetrical about an axis of symmetry 22 through the center of the bearing 14. A wedge ring or adapter ring 24 is situated between the base cup 12 and the bearing 14. Adapter ring 24 is tapered or non-symmetrical so that when it is mounted on the base cup 12 in selectively variable positions, the adapter ring 24 will present the symmetrical bearing 14 in various positions relative to the base cup 12. By rotating the adapter ring 24 relative to the axis of symmetry 20 of base cup 12, an orthopedic surgeon installing the cup assembly 10 can easily align the bearing 14 in a plurality of angular positions with respect to base cup 12 after the base cup 12 is firmly attached to the acetabulum. By changing the angular position of the bearing 14, the surgeon can align the bearing surface 16 so that it is in a better position to receive femur ball 18. The term angular positions, as shown in the drawings, can be defined as the diametrical plane defining the hemispherical portion of the bearing surface being angled with respect to the diametrical plane defining the hemispherical portion of the base cup.

Adapter ring 24 is generally circular and includes a first planar mating surface 26 configured to abut the lip or rim 28 of base cup 12. The rim 28 defines a plane through which bearing 14 enters cavity 13 of base cup 12. Rim 28 is formed to include a plurality of openings 30 which may illustratively be threaded for receiving suitable fasteners such as screws 32.

Adapter ring 24 also includes a second planar mating surface 34 for abutting the underside of flange 36 of bearing 14. The planar flange 36 of bearing 14 defines a plane through which femur ball 18 enters bearing surface 16. Adapter ring 24 is formed to include three equally spaced apertures 38, and flange 36 of bearing 14 is formed to include three equally spaced apertures 40 which are aligned with apertures 38 of adapter ring 24. It is understood that the number and position of the apertures 38 and 40 may be changed.

As shown in FIGS. 1 and 2, by disposing the adapter ring 24 between the symmetrical base cup 12 and the symmetrical bearing 14, the axis of symmetry 20 of base cup 12 is aligned at a pre-determined angle with respect to the axis of symmetry 22 of bearing 14. This pre-determined angle is illustrated by arrows 42.

Adapter ring 24 can be rotated with respect to base cup 12 so that the apertures 38 are aligned with any selected openings 30 in base cup 12. This provides the surgeon with a plurality of positions for the adapter ring 24 to change the position of the bearing 14 once the base cup 12 is attached to the acetabulum. Bolts or screws 32 extend through apertures 40 of bearing 14, through apertures 38 of adapter ring 24, and into threaded openings 30 of base cup 12. The symmetric bearing 14 is inserted through the adapter ring 24 and into base cup 12 in only one orientation after the adapter ring 24 is rotated to a selected position.

FIG. 2 shows the femur ball 18 abutting the bearing surface 16 of bearing 14. The femur ball 18 is connected to a neck 44 and stem 46 which is designed to be attached to a femur (not shown). The cup assembly 10 permits the symmetrical bearing 14 and the symmetrical base cup 12 to take on characteristics of a non-symmetrical cup assembly by disposing the adapter ring 24 between the base cup 12 and the bearing 14.

Bearing 14 is preferably made from a polymeric material such as ultra high molecular weight polyethylene (UHMWPE). The symmetrical bearing 14 is inherently stronger than non-symmetrical bearings shown in the prior art.

Figure 4:
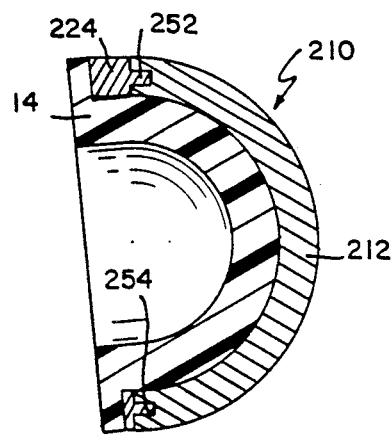

The adapter ring 24 of the cup assembly 10 may be formed to include some type of track assembly to facilitate rotation of the adapter ring 24 with respect to the base cup 12. FIGS. 3 and 4 illustrate two types of rabbet or track configurations for facilitating rotational movement of the adapter ring with respect to the base cup. In the remaining embodiments of the present invention shown in FIGS. 3-10, those elements referenced by numbers identical to those used in FIGS. 1 and 2 perform the same or similar function.

In the embodiment of the invention shown in FIG. 3, the cup assembly 110 includes a base cup 112, an adapter ring 124 and a bearing 14. A flange 148 extends from the inner diameter of adapter ring 124 engages a recess 150 formed in base cup 112.

In the embodiment of the invention shown in FIG. 4, the cup assembly 210 includes a base cup 212, an adapter ring 224 and a bearing 14. A track 252 extends from adapter ring 224 and engages an arcuate groove 254 formed in base cup 212. These track configurations shown in FIGS. 3 and 4 permit the surgeon to easily dial or rotate the adapter rings 124 and 224, respectively, to a selected orientation or position with respect to base cups 112 and 212 after the base cups 112 and 212 are rigidly attached to the acetabulum. After the adapter rings 124 and 224 are rotated to their selected positions, bearings 14 and adapter rings 124 and 224 are secured to the base cups 112 and 212 by suitable fasteners 32 (not shown in FIG. 4).

Another embodiment of the present invention is shown in FIG. 5. In this embodiment, the cup assembly 310 includes a base cup 312, an adapter ring 324, and a bearing 14. A plurality of lugs 356 are formed on the first mating surface 326 of adapter ring 324. The base cup 312 is formed to include a plurality of notches 358 spaced along the rim 328 of base cup 312. The notches 358 are configured to receive the lugs 356 of adapter ring 324 to position the adapter ring 324 in the selected orientation relative to the base cup 312.

Although FIG. 5 illustrates six lugs 356 and notches 358, it is understood that the number of lugs 356 and notches 358 may be changed to any suitable number. There may also illustratively be fewer lugs 356 than notches 358. The lugs 356 and notches 358 help hold the adapter ring 324 in position on the base cup 312 while the bearing 14 is inserted into cavity 313 of base cup 312 prior to securing bearing 14 and adapter ring 324 to the base cup 312 with fasteners 32.

FIGS. 6 and 7 illustrate yet another embodiment of the present invention. Cup assembly 410 includes a base cup 412, an adapter ring 424, and a bearing 14. This embodiment is similar to the embodiment shown in FIGS. 1 and 2 but uses a different method of attaching the bearing 14 and adapter ring 424 to the base cup 412. The base cup 412 in FIG. 6 is formed to include a plurality of rectangular shaped apertures 460. Clips 462 are used to secure bearing 14 and adapter ring 424 to base cup 412. The clips 462 include first and second projections 464 and 466. The projections 464 and 466 can be compressed so that the projections pass through apertures 40 formed in bearing 14, apertures 438 in adapter ring 424, and openings 430 in base cup 412. When the ends of projections 464 and 466 pass into rectangular opening 460 of base cup 412, they expand outwardly to engage the rectangular aperture 460 and secure the clips 462 in position. FIG. 7 illustrates the clip 462 after the projections 464 and 466 have expanded inside rectangular aperture 460 to secure the bearing 14 and adapter ring 424 to the base cup 412. It is understood that aperture 460 may be shaped in any desired configuration for receiving the clip 462. The shape of aperture 460 is not limited to the rectangular configuration shown in FIG. 7.

Still another embodiment of the present invention is shown in FIGS. 8 and 9. In this embodiment, a bayonet and castellation attachment device 568 is used to secure a bearing 514 and adapter ring 524 to base cup 512. The attachment device 568 includes a main shaft 570 and a cross member 572. The attachment device 568 also includes a castellation 574 for connecting the bearing 514 to the base cup 512.

The attachment device 568 is inserted through an aperture 576 in adapter ring 524 and into an opening 578 in base cup 512. A suitable tool (not shown) is used to rotate the attachment device 568 90° to lock the device 568 inside opening 578. The bearing 514 which is similar to the bearing 614 shown in FIG. 10 is then locked in place over castellation 574.

A further embodiment of the present invention is shown in FIG. 10. In this embodiment, the cup assembly 610 includes a base cup 612, an adapter ring 624, and a bearing 614. A castellation 674 is formed directly on the adapter ring 624. When the adapter ring 624 is secured in its selected orientation on the base cup 612 by fasteners 32, the bearing 614 which includes a notch 676 can be inserted over the castellation 674 to secure the bearing 614 to the adapter ring 624. FIG. 10 clearly shows that the bearing 614 is inserted into base cup 612 in only one orientation with respect to adapter ring 614 and base cup 612.

Although the invention has been described in detail with reference to several preferred embodiments, variations in modifications exist within the scope and spirit of the invention as described and defined in the following claims.

We claim:

1. An acetabular cup prosthetic assembly for receiving a ball attached to a femur, said assembly comprising
   a base cup to be affixed to the acetabulum generally in the position of the natural socket to be replaced, said base cup having a generally hemispherical cavity opening toward said ball,
   a bearing disposed in said cavity to provide a hemispherical bearing surface for said ball, and
   an adapter ring means positionally mounted on said base cup about said cavity for positioning a diametrical plane that defines the end of the hemispherical surface of said bearing in a selected angular position relative to a diametrical plane that defines the generally hemispherical cavity of said base cup in accordance with mounting position of said adapter ring means,
   said adapter ring means being mounted at one of a plurality of selected positions about the axis of said base cup, and
   said adapter ring means being formed such that according to the selected mounting position on said base cup used to mount the adapter ring means, the adapter ring means will alter the selected angular position of said diametrical plane of said bearing relative to said axis and plane of said base cup.

2. The assembly of claim 1, wherein said base cup is formed to include a mounting surface about a periphery of said hemispherical cavity, means for rotatably coupling said adapter ring means to said mounting surface to permit rotation of said adapter ring means about said axis of said base cup to orient said adapter ring means into the one selected mounting position.

3. The assembly of claim 2, further comprising means for rigidly securing said adapter ring means to said base cup after said adapter ring means is oriented in its selected mounting position.

4. The assembly of claim 3, wherein said means for rigidly securing includes a plurality of screws extending through said bearing and said adapter ring means and into the said mounting surface of said base cup.

5. The assembly of claim 3, wherein said mounting surface is formed to include track means for receiving a portion of said adapter ring means to permit rotation of said adapter ring means about said axis of said base cup.

6. The assembly of claim 5, wherein said securing means includes at least one pin in member extending through said adapter ring means and engaging said base cup to hold said adapter ring means in its selected position.

7. The assembly of claim 6, wherein said pin member includes a cross member for locking said pin member in said base cup and a castellation for securing the bearing to said adapter ring means.

8. The assembly of claim 5, wherein said securing means includes a clip member configured to extend through said adapter ring means and to engage a portion of said base cup to prevent rotation of said adapter ring means relative to said base cup when said adapter ring means is in its selected mounting position.

9. The assembly of claim 2 wherein said coupling means includes a bayonet attachment formed on said adapter ring means, and said base cup is formed to include a groove in said cavity configured to receive said bayonet attachment to permit rotation of said adapter ring means relative to said axis of said base cup while holding said adapter ring means on said mounting surface.

10. The assembly of claim 1, wherein said adapter ring means is formed to include a castellation for securing said bearing to said adapter ring means.

11. A hip prosthesis for receiving a ball attached to a femur to replace the natural ball, the prosthesis comprising a base cup for attachment to an acetabulum to replace a natural hip socket, bearing means for holding said ball in said base cup, means for mounting said bearing means on said base cup, and means for attaching said mounting means in one of a plurality of selected mounted positions on said base cup, said mounting means being non-symmetrically shaped such that it will selectively and angularly tilt said bearing means on said base cup in different angular tilted positions determined by the selected mounting position of the mounting means so that an axis of the bearing means is tilted at different angles with respect to an axis of the base cup.

12. The prosthesis of claim 11, wherein said base cup has an inner surface defining a symmetrical hemispherical cavity and said bearing means has an inner surface defining a symmetrical cavity for receiving said ball.

13. The prosthesis of claim 12, wherein said mounting means includes a wedge-shaped adapter ring and said base cup is formed to include a mounting surface for abutting a portion of said adapter ring to permit said adapter ring to be mounted on said base cup in a plurality of selected orientations.

14. The prosthesis of claim 13, wherein said mounting surface is formed to include a plurality of notches configured to receive a plurality of lugs formed on said adapter ring to position said adapter ring in one of said selected orientations.

15. The prosthesis of claim 13, wherein said mounting surface is formed to include track means for permitting said adapter ring to rotate about said mounting surface to position said adapter ring in its selected orientation.

16. An acetabular cup assembly for receiving a ball attached to a femur, the assembly comprising a symmetrical bearing having a bearing surface for receiving the ball, the bearing surface having an axis symmetry, a symmetrical base cup for attachment to the acetabulum to replace a natural socket, the base cup having a surface for receiving the bearing, the base cup surface having an axis symmetry, an adapter ring angularly disposed between the bearing and the base cup to align the axis of the bearing positionally at one of a number of different predetermined tilted angles with respect to the axis of the base cup in accordance with an angular disposition of the adapter ring with respect to the bearing.

17. The assembly of claim 16, including means for rotatably coupling the adapter ring to the symmetrical base cup so that the adapter ring can be rotated relative to the axis of the base cup to change said angular disposition and the angle of the axis of the bearing with respect to the axis of the base cup after the base cup has been attached to the acetabulum.

18. The assembly of claim 17, wherein the base cup includes a circular mounting surface formed to include a plurality of apertures and the adapter ring is formed to include at least two apertures which can be aligned with apertures in the mounting surface so that at least two fasteners can extend through the at least two apertures formed in the adapter ring and into the apertures in the mounting surface to rigidly secure the adapter ring to the base cup.

19. The assembly of claim 18, wherein the plurality of apertures formed in the mounting surface base cup are threaded to receive screws which extend through the apertures in the adapter ring to rigidly secure the adapter ring to the base cup.

20. The assembly of claim 16, wherein the adapter ring includes a first mating surface situated in a first plane for engaging the base cup and a second mating surface situated in a second plane for engaging the bearing, the first plane being situated at a dihedral angle with respect to the second plane to align the axis of the bearing at the predetermined angle with respect to the axis of the base cup.

21. The assembly of claim 16, wherein the symmetrical bearing has a limited orientation with respect to the base cup along a single plane and the adapter ring rotates about the axis of the base cup to change the angle of the bearing with respect to the base cup after the base cup is attached to the acetabulum.

22. A prosthetic hip cup assembly for receiving a ball attached to a femur and connecting the ball to an acetabulum, the assembly comprising a bearing having a bearing surface for receiving the ball and an outer flange defining a plane through which the ball enters the bearing surface, a base cup for attachment to the acetabulum, the base cup having a cavity for receiving the bearing and an outer mounting surface defining a plane through which the bearing enters the cavity, and adapter means, attached to the cup in one of a plurality of positions for positioning the bearing in the cavity of the cup to align the plane of the bearing at a preselected dihedral angle with respect to the plane of the base cup in response to the particular attachment position of the adapter means.

23. The assembly of claim 22, wherein the adapter means includes a wedge-shaped adapter ring coupled to the base cup in a plurality of selected orientations to change the position of the bearing with respect to the base cup after the base cup is attached to the acetabulum.

24. The assembly of claim 23, wherein the adapter ring is rotatably coupled to a mounting surface of the base cup so that the adapter ring can be rotated along the mounting region of the base cup.

25. The assembly of claim 24, further comprising means for rigidly securing the adapter ring to the base cup after the adapter ring is situated in its selected orientation.

26. The assembly of claim 22, wherein the base cup has an inner surface symmetrical hemispherical cavity for receiving the bearing and the bearing has an inner surface symmetrical cavity for receiving the ball.

27. An acetabular cup assembly for receiving a ball attached to a femur, the assembly comprising a symmetrical bearing having a surface for receiving the ball, the bearing surface having an axis symmetry, a symmetrical base cup for attachment to the acetabulum to replace a natural socket, the base cup having a surface for receiving the bearing, the base cup surface having an axis symmetry, an adapter ring disposed between the bearing and the base cup to align the axis of the bearing at a predetermined angle with respect to the axis of the base cup, wherein the adapter ring includes a first mating surface situated in a first plane for engaging the base cup and a second mating surface situated in a second plane for engaging the bearing, and wherein the first plane is situated at a dihedral angle with respect to the second plane to align the axis of the bearing at the predetermined angle with respect to the axis of the base cup.

28. The assembly of claim 27, wherein the symmetrical bearing has a limited orientation with respect to the base cup along a single plane and the adapter ring rotates about the axis of the base cup to change the angle of the bearing with respect to the base cup after the base cup is attached to the acetabulum.

29. A prosthetic hip cup assembly for receiving a ball attached to a femur and connecting the ball to an acetabulum, the assembly comprising a bearing having a bearing surface for receiving the ball and an outer flange defining a plane through which the ball enters the bearing surface, a base cup for attachment to the acetabulum, the base cup having a cavity for receiving the bearing and an outer mounting surface defining a plane through which the bearing enters the cavity, and adapter means for mounting the bearing to the cup to align the plane of the bearing at a preselected dihedral angle with respect to the plane of the base cup, wherein the adapter means includes a wedge-shaped adapter ring coupled to the base cup in a plurality of selected orientations to change the position of the bearing with respect to the base cup after the base cup is attached to the acetabulum.

30. The assembly of claim 29, wherein the adapter ring is rotatably coupled to a mounting surface of the base cup so that the adapter ring can be rotated along the mounting region of the base cup.

31. The assembly of claim 30, further comprising means for rigidly securing the adapter ring to the base cup after the adapter ring is situated in its selected orientation.

* * * * *

UNITED STATES PATENT AND TRADEMARK OFFICE
CERTIFICATE OF CORRECTION

PATENT NO. : 5,002,577

DATED : March 26, 1991

INVENTOR(S) : Bolesky et al.

It is certified that error appears in the above-identified patent and that said Letters Patent is hereby corrected as shown below:

In column 6, line 31, after "and", please insert --diametrical--

In column 6, line 52, please delete "in".

Signed and Sealed this

Third Day of November, 1992

Attest:

DOUGLAS B. COMER

Attesting Officer

Acting Commissioner of Patents and Trademarks